(12) United States Patent
Vetrecin

(10) Patent No.: US 8,865,247 B2
(45) Date of Patent: Oct. 21, 2014

(54) NEEDLE COATING FORMULATION HAVING LUBRICITY AND DURABILITY

(75) Inventor: Robert Vetrecin, Stewartsville, NJ (US)

(73) Assignee: Ethicon, Inc., Somerville, NJ (US)

( * ) Notice: Subject to any disclaimer, the term of this patent is extended or adjusted under 35 U.S.C. 154(b) by 993 days.

(21) Appl. No.: 12/642,373

(22) Filed: Dec. 18, 2009

(65) Prior Publication Data

US 2011/0152926 A1   Jun. 23, 2011

(51) Int. Cl.
*A61L 33/00*  (2006.01)
*A61K 9/14*  (2006.01)
*C08F 8/00*  (2006.01)
*A61B 17/06*  (2006.01)
*C09D 183/04*  (2006.01)
*B05D 5/08*  (2006.01)

(52) U.S. Cl.
CPC ............ *A61B 17/06* (2013.01); *C09D 183/04* (2013.01); *B05D 5/08* (2013.01)
USPC .............................. 427/2.1; 424/486; 525/100

(58) Field of Classification Search
None
See application file for complete search history.

(56) References Cited

U.S. PATENT DOCUMENTS

| | | | | |
|---|---|---|---|---|
| 3,932,555 A | * | 1/1976 | Goodrich et al. | 525/29 |
| 4,331,715 A | * | 5/1982 | Wolpert | 427/240 |
| 6,558,409 B1 | | 5/2003 | Roby | |
| 7,041,088 B2 | | 5/2006 | Nawrocki | |
| 2003/0171777 A1 | | 9/2003 | Roby | |
| 2005/0142079 A1 | * | 6/2005 | Garrison et al. | 424/59 |
| 2006/0019004 A1 | | 1/2006 | Beelman | |
| 2006/0127681 A1 | * | 6/2006 | Domes et al. | 428/447 |

\* cited by examiner

*Primary Examiner* — Scott Long
*Assistant Examiner* — Lyndsey Beckhardt
(74) *Attorney, Agent, or Firm* — E. Richard Skula

(57) ABSTRACT

A medical device coated with a novel lubricious coating is disclosed. The coating contains a pre-oxidized hydrophobic polymer, a cross-linking agent, a silicone or siloxane polymer, a slip agent and a catalyst.

6 Claims, 4 Drawing Sheets

NEEDLE COATING FORMULATION HAVING LUBRICITY AND DURABILITY

FIELD OF THE INVENTION

The present invention is directed to coatings for medical devices, in particular, lubricious coatings for medical devices.

BACKGROUND OF THE INVENTION

It is known in this art to provide lubricious coatings for medical devices. Lubricious coatings are typically required for implantable or insertable medical devices such as hypodermic needles, surgical needles, trocar obturators, cutting devices, penetrating devices and catheters that are in contact with tissue. The primary purpose of such coatings is to ease the penetration or implantation of the device into tissue, often for multiples passes, cycles or cuts, e.g., surgical needles and scalpels.

Surgical needle and suture combinations are the mainstay of most surgical procedures. Conventional surgical needles are elongated members having curved configurations, distal piercing tips and proximal suture mounting ends. The surgical needles may have optional cutting edges as well. The suture mounting ends may consist of formed channels or drilled bore holes in which the end or ends of a surgical suture is mounted. The function of the surgical needles is to pierce, and in certain instances pierce and cut, tissue to create a channel or pathway for the surgical suture through tissue that the surgeon desires to approximate. Typically, multiple passes of the needle and suture through tissue are required to effectively approximate tissue surrounding a wound or opening, or to affix a prosthetic device such as a heart valve to tissue, etc. The suture frequently forms conventional stitches that are secured with conventional surgeon's knots.

As previously mentioned, it is known to coat surgical needles with conventional lubricious coatings. Such coatings include polymeric silicones and siloxane, including polymers such as polydimethylsiloxane, having various different end groups, molecular weight, along with additives such as cross-linkers, catalysts, etc. These additives to the coating ensure that the silicones have adequate adhesion and durability when used as a needle coating. Silicone coatings for medical devices including surgical needles are disclosed in U.S. Pat. No. 7,041,088 which is incorporated by reference.

It is know that surgical needles may experience diminished penetrative ability with each pass through tissue, possibly resulting in inconsistent performance. While the application of coatings (silicones, in particular) to needles often provides lubricity and durability, thereby extending their useful life, the application of the coatings may require a time-consuming process involving the deposition of a silicone solution and subsequent curing, including the evaporation of solvent(s), and thermal treatment. Although surgical needles have benefited from presently used coatings, there is a constant need in this art for further improvements that may enhance the use of surgical needles by surgeons in surgical procedures. In particular there is a need for improved lubricious coatings having improved characteristics including lubricity to reduce insertion and drag forces, durability to maintain the penetration performance, long term stability (package/or storage), biocompatibility, ease and efficiency of application and compatibility with sterilization method.

SUMMARY OF THE INVENTION

Accordingly, a medical device coated with a novel lubricious coating is disclosed. At least one surface of the medical device is at least partially coated with the coating. The coating consists of a mixture of a silicone polymer, a silicone cross-linking agent, a pre-oxidized hydrophobic polymer, a catalyst, a slip agent and compatible solvents.

Another aspect of the present invention is a method of coating a surface of a medical device with the previously described coating.

These and other aspects of the present invention will become more apparent from the following description and accompanying drawings.

DETAILED DESCRIPTION OF THE INVENTION

Figure 1:
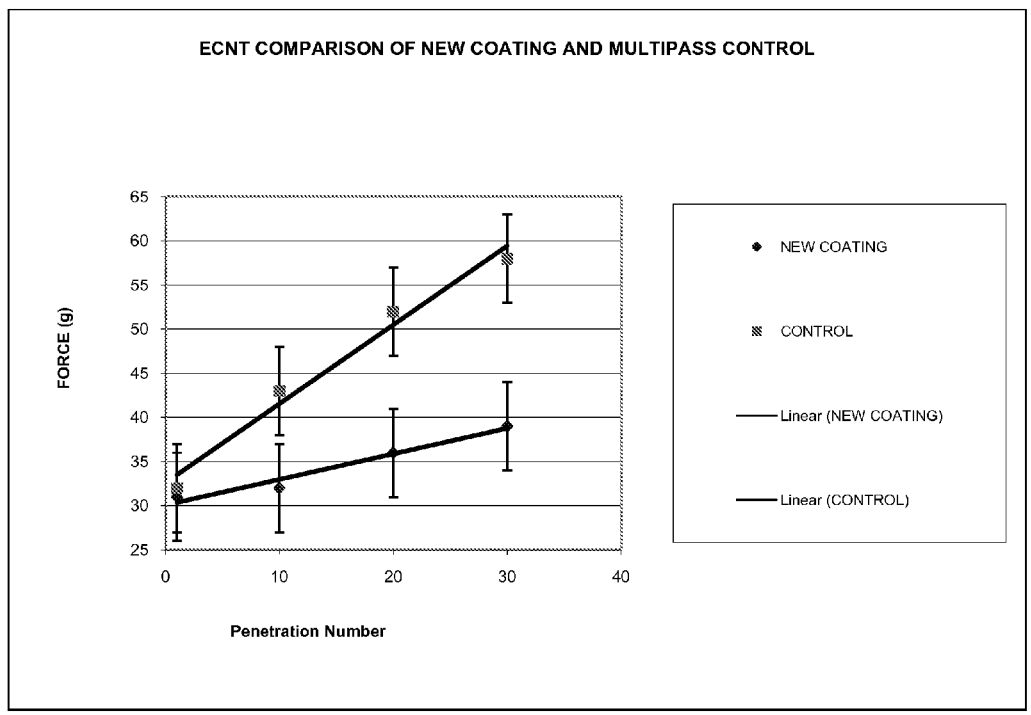
FIG. 1 is a graph illustrating the effect on needle penetration performance of the coating of the present invention compared to a state of the art, commercially available needle coating.

The medical devices that can be coated with the novel coatings of the present invention include conventional medical devices and equivalents thereof, which have surfaces that come into contact with tissue. In particular, the novel lubricious coatings of the present invention are useful with devices having surfaces that come into contact with tissue wherein the device is inserted into and passed through or implanted in tissue. Examples of devices having tissue contact surfaces that can be coated with the novel, lubricious coatings of the present invention include surgical needles, hypodermic needles, catheters, trocars, obturators, scalpels, and other penetrating, cutting or implantable devices. It is particularly preferred to use the coatings of the present invention to coat tissue contact surfaces of conventional surgical needles. The surgical needles will typically have an elongated member having a distal piercing point extending from a distal end and a proximal suture mounting end. The distal piercing point may have a variety of conventional configurations, including various taper and cutting edge geometries. In addition, the ratio of the taper length to diameter can vary up to but not necessarily limited to 12 to 1. The surgical needle may also optionally have conventional cutting edges. The proximal suture mounting ends can consist of conventional mounting configurations including drilled bore holes and coined or formed channels. The elongate member may have a variety of central cross-sections along its length including round, I-beam, square, tapered, etc.

The medical devices that can be coated using the coatings and processes of the present invention may be formed from various conventional biocompatible materials including, without limitation, austenitic or martensitic stainless steels such as 304ss, 316ss, 420ss, 455ss, ETHALLOY (or any stainless steel described in ASTM F 899), refractory alloys, ceramics or biocompatible polymers including polyolefines or florinated polymers such as polyvinylidene fluoride.

The novel lubricious coating compositions of the present invention will contain sufficient amounts of silicone polymer to effectively provide a uniform coating of sufficient thickness and functionality on the medical 1 device. The silicone polymers used in the coating compositions include conventional silicone polymers of varying molecular weight and functionality. The preferred polymeric silicones are the polysiloxanes and, in particular, the polyalkylsiloxanes. Conventional biocompatible silicones are available for coatings with various molecular weights, end groups chemistry and functional grafting for use as a coating. A preferred alkyl siloxane is polydimethylsiloxane (PDMS). The polydimethyl siloxanes are typically supplied with proprietary end-group chemistry to facilitate bonding to a metal substrate and sold as "lubricious silicone" coatings. The PDMS (polydimethylsiloxane) can be vinyl terminated, hydroxyl terminated, or amine terminated. They must also be capable of cross-linking for stability and durability. The most preferred silicone polymer is polydimethylsiloxane that is hydroxyl terminated such as MED4162 supplied by NUSIL Technology, Caprenteria, Calif. Coating compositions of the present invention will generally contain about 4 wt. % to about 10 wt. % of the total weight of the coating solution, more typically about 4 wt. % to about 8.4 wt. %, and preferably about 6 wt. % to about 8.4 wt. %.

The novel lubricious coating compositions of the present invention will also contain sufficient amounts of at least one cross-linking agent to effectively provide durability of the coating through multiple passes through tissue. The cross-linking agents include methyl hydrogen polydimethyl siloxane, tetraethyl siloxane or any conventional biocompatible agent capable to chemically linking siloxane polymeric chains. The preferred formulation will contain methyl hydrogen polydimethyl siloxane at varying molecular weights up to but not limited to 10,000 Daltons. The concentrations of the cross-linking agent used in a coating formulation of the present invention are calculated on the weight of silicone and expressed as a weight percent. The ratio of cross-linker to siloxane is typically about 1.0 wt. % to about 10.0 wt. % of the weight of siloxane. A preferred ratio of cross-linker to siloxane is about 2.0 wt. % to about 8.0 wt. %. The most preferred ratio for a cross-linking agent that is a hydroxyl terminated polydimethylsiloxane, such as MED4162 supplied by NUSIL Technology, is about 6.0 wt. %.

The catalysts useful in the coatings of the present invention will include conventional silicone coating catalysts (platinum, tin or titanium complexes) including dibutyl tin dilaurate, stannous octoate or organo-platinum catalysts. The degree of cross-linking is a function of the concentration of cross-linker, catalyst and temperature of the cross-linking reaction, and can be adjusted to accommodate the substrate and application process. For example, stannous octoate can be used up to but not limited to about 20.0 wt % to about 30.0 wt %, dibutyl tin dilaurate can be used in this range at reaction temperatures up to 150° C. and organo-platinum catalysts at the parts per million concentration range can also be used at temperatures over 100° C. The preferred catalyst system is a dibutyltin dilaurate at a concentration of about 0.1 wt. % of the silicone weight.

The novel lubricious coating compositions of the present invention will also contain a sufficient amount of an oxidized hydrophobic polymer to effectively react with the cross-linking agent to provide a composite matrix after reaction. The resulting composite matrix results in a toughened coating that is more durable than a non-composite coating.

The hydrophobic polymer is a polymer that lacks affinity for water and is readily recognized by those skilled in the art. More specifically, we believe a hydrophobic polymer as it relates to this invention is a polymer with a surface energy of less than 50 mN/m. In the preferred embodiment of this invention the hydrophobic polymer is a thermoplastic polymer. Preferably the polymer has a melting, softening, glass transition temperature that is sufficiently low to flow at the temperature necessary to cure the silicone portion of the coating. Consequently, the hydrophobic polymer ideally has a melting point less than about 210° C. or a glass transition temperature less than 100° c. in the case of amorphous hydrophobic polymers. Examples of non-silicone, hydrophobic polymers that can be used include but are not limited to polypropylene, polyethylene, and polycaprolactone, and combinations thereof and equivalents. The non-silicone hydrophobic powders can be in the form of a solid and in particular in the form of a micronized powder. The most preferred non-silicone, hydrophobic polymer is a polypropylene wax of varying molecular weight such as Micromatt-2000 and Micropro 600.produced by Micropowders, Inc., Tarrytown, N.Y. These polymers are a mixture of semi-crystalline moieties that have melting temperatures between 90° C. and 175° C. with a median particle size of 6 to 9 microns.

The coating compositions will typically contain about 2.0 wt. % to about 3.0 wt. % of the oxidized hydrophobic polymer, more typically about 2.6 wt. % to about 3.0 wt. %. The concentration of the hydrophobic polymers is calculated as a weight percent of the total weight of coating solution.

Before incorporation into the coating solution, the polymer powders of the present invention are exposed to heat and oxygen in order to have a pre-formed oxidized surface layer. This layer manifest itself after heat treatment of the powder, for example at 115° C., and appears as a light brown patina on the surface of the particles, which are nominally white in the untreated condition. During the heat treatment, volatilization of a low molecular weight component may occur as noted by the presence of a distinct waxy odor. Oxidation of the powders also takes place. This can be determined qualitatively using a Diamond Anvil FTIR and manifest itself by the appearance of the carbonyl absorbance at 1749 cm-1. (Liebert, Chartoff, Cosgrove, "Subcutaneous Implants of Polypropylene Filaments, J. BIOMED. MATER. RES. Vol. 10, pp. 939-951.)

The hydrophobic polymers used in the coatings of the present invention are preferably heat treated in a conventional oven at 115° C. in air for fourteen hours, however those skilled in the art will appreciate that other treatment regimens may be used. After cooling, the powders are blended and then preferably milled in a ball mill containing ceramic media for up to fourteen hours. These hydrophobic polymers are preferably used in a powder form but other physical forms of the polymers may be utilized including dissolution of the polymers in a hot aromatic solvent to facilitate blending with the silicone coating component. When used in this manner, the coating solution is applied hot to facilitate uniform coating of the device. The powdered hydrophobic polymers will have a particle size distribution that is effective to allow the powders to be fully dispersed without clumping in the coating solution. Typically, the particle size distribution following milling will be between about 2 microns to about 110 microns, more typically about 10 microns to about 90 microns, and preferably about 28 microns to about 70 microns as measured by a Beckman Coulter LS Particle Size Analyzer in HFE solvent.

The novel lubricious coating compositions of the present invention will also contain a sufficient amount of a slip agent to effectively provide ease of tissue passage for the medical device. The slip agents useful in the coating compositions of the present invention are common additives that are added to silicones to improve their lubricity. These slip agents include but are not limited to distearate polydimethylsiloxane, lithium stearate, zinc stearate, and calcium stearate. Most preferably the slip agent will be a disterate polydimethyl siloxane. The coating compositions will typically contain about 2.0 wt. % to about 8.0 wt. % of the slip agent, more typically about 5.0 wt % to about 6.0 wt. %, and preferably about 5.0 wt. %. The concentration of slip agent is a weight percent calculated on the total weight of coating solution.

The solvents used to mix and apply the coating can be any common, conventionally-used solvent for silicone polymers, including an aromatic solvent, (xylene, benzene, toluene), a volatile alkane such as hexane, heptanes, etc. The lower molecular weight, volatile solvents are quite volatile and are generally avoided in practice. A preferred solvent to blend the components of the coating is a high molecular weight alkane such as EXXON Isopar-K. Isopar K is a less volatile, higher boiling solvent more suitable for manufacturing operations. This solvent is added at a concentration sufficient to allow blending of the components comprising the coating solution. Typically, a sufficient amount of solvent is used to provide effective mixing and coating characteristics to the coating mixture, for example ant amount of solvent present may be about 73.0 wt. % by weight of the mixture.

The coatings compositions are prepared in the following manner The coating compositions of the present invention can be prepared by mixing the previously mentioned components in a conventional mixing apparatus, for example, an apparatus that utilizes a high shear impeller (blade). Such conventional apparatuses include conventional high shear mixing apparatus such as a Cowles mixer or high shear homogenizer. If conventional mixing is used the sequence of the addition of the components is important. For conventional mixing, the total amount of solvent used for the coating is added to the mixing vessel first. Then the prescribed amount of silicone coating polymer (e.g., MED 4162) is dispersed into the solvent. Once dispersed, the slip agent, e.g., disterate polydimethylsiloxane, is added to the mixture. Once this is dissolved, the prescribed amount of pre-oxidized hydrophobic powders is slowly added to the stirred solution to avoid clumping. Mixing continues for a sufficient time to provide effective dispersion in the coating composition after addition of the powders, for example, for up to five hours. Ball milling of the components is the preferred method of blending of the coating. If this technique is used, all of the weighed components of the coating are added together into a suitable sized milling crock. Adequate mixing agate is added to the crock and the crock is sealed. The mixture is milled for at least ten hours. The solvents used in the blending process can be any aromatic or alkane solvents that the components are soluble in that results in appropriate surface tension of the coating solution. Certain fluoroether azeotropes can also be used as the solvent to provide a less flammable coating solvent system.

The novel lubricious coating compositions of the present invention are applied to the surfaces of a medical device using conventional coating techniques and processes and conventional coating process equipment. The coating equipment that can be used to coat the coated medical devices of the present invention includes simple dip coating tanks and air and heat drying apparatus. Coatings can be applied by brushing, rolling or spraying processes. The cross-linking reaction can be carried out either in an air, nitrogen or vacuum oven at temperatures between 140° C. and 200° C. A preferred temperature is 195° C. for at least one hour and up to four hours. Although the coatings of the present invention may be applied as a single coating layer to a surface of a medical device, it may also be advantageous to apply multiple coating layers depending upon factors such as device material, surface characteristics, usage, device geometry, etc.

The following examples are illustrative of the principles and practice of the present invention although not limited thereto.

Example 1

Preparation of Coating

A typical coating solution of the present invention was prepared in the following manner.

A master batch of MicroMatte and MicroPro was prepared by blending 210 grams of MicroPro 600 with 50 grams of Micro Matte 2000. After blending, the powder was placed in a 115° C. oven for fourteen hours. Following the heat-treat cycle, the cooled powder blend was transferred to a ball mill of sufficient capacity to contain the entire sample. Agate was added to the crock and the crock sealed. It was then placed on a tumbling machine and allowed to rotate at a low rpm for at least five and as long as fourteen hours to yield a uniform finely ground powder.

A production sized blend of the powder was prepared as follows. Weighed0 into a large ball mill crock were 165 grams MED4162, 420 grams Isopar K, 15.6 grams heat treated and milled powder, and 31 grams di-stearate PDMS. This mixture was blended in the ball mill for up to 14 hours to a uniform dispersion of exceptional stability that did not readily settle out. The blend was then ready for use and was stable for more than a week.

The oxidation process was initiated by blending polymeric powder (a combination of MicroMatte and MicroPro was used), and then oxidizing it in air at 105° C. After the heat treatment, the polymers were ground in a conventional ball mill for several hours to a uniform powder. Into another ball mill, a solution of MED1-4162 coating solution was weighed along with the prescribed amount of Isopar K. This was followed by the addition of the blended, heat-treated polymeric powders that were added to the mixture at a concentration of 2.6 wt % of the total weight of the coating solution. Then added was 2.0 wt. % of the total weight of the coating solution of methyl hydrogen polydimethylsiloxane. Next, 5.0 wt. % of di-stearate PDMS was added. All of the components were then blended in a ball mill to ensure uniform particle size of the polymeric powder and uniform dispersal in the coating solution

Example 2

Application of Coating

A weighted aliquot of the prepared coating of Example 1 was transferred to a conventional dip tank. The silicone content of the aliquot was determined Dibutyltin dilaurate at a concentration of 0.1 wt. % of the silicone weight was added to the tank with stirring via a conventional agitator. The catalyzed mixture was stable for at least 24 hours.

Surgical needles were coated from this solution by dipping or a moving curtain of the mixture. When using only a single dip, the needles were air dried and then the coating was reacted at a temperature of 195° C. for one hour and not more than four hours in a conventional air or vacuum oven. When a second dip was required, the coated needles were re-dipped and air dried a second time followed by the same heat treatment as for the single dip.

Example 3

Testing of the Coating

The test methods used to measure the force to penetrate a synthetic substrate representative of soft tissue (Ethicon Curve Needle Tester) or the force to push the needle through the same or similar substrate (body drag). Standard Ethicon, Inc BV-175 Needles were coated and used for the testing. Ten needles were penetrated thirty times for each coating. Further details of the test equipment and method can be found in U.S. Pat. No. 5,181,416 and "A synthetic membrane for testing needle penetration". J. of Appl Biomaterials 1993; 4: 157-160, which are incorporated by reference.

In the case of the curved needle tester used for surgical needles, coating performance and integrity was evaluated using the penetration test device. A coated surgical needle was held using self-locking tweezers or a similar holding device. The coated needle was then passed through a media that is representative of general human tissue. The entire needle was not passed through the media, but only approximately half of each needle was passed through the test media. The needle was then retracted. A new area was selected on the test media and the penetration sequence was repeated for up to thirty times. Peak force was noted for each penetration and was characteristic of the lubricity and durability of the coating being tested. Further details of the test equipment and method can be found in U.S. Pat. No. 5,181,416 which is incorporated by reference.

Body Drag was determined using a TA.XT.PLS Texture Analyzer equipped with suitable grips to hold a straight 22 mil taper pointed needle. Test media was mounted on a test ring to facilitate the needle penetration force and drag. The synthetic test media used is representative of general human tissue. For this test, ten coated needles were passed through the test media ten times each. The constant force associated with body drag as the needle passed through the test media was noted and is characteristic of the lubricity and durability of the coating on the needle. A new area on the test media was selected for each penetration.

FIGS. 1-4 graphically present the results of the testing of various coatings as described in Examples 1 and 2 and as applied to surgical needles. Test results are the average from ten needles penetrated ten times.

As shown in FIG. 1, the force needed to penetrate through a simulation substrate with needles treated with the coating of the present invention was observed to be significantly reduced compared with needles not treated with the coating of the present invention. It is noted that the reduction effect was more profound with increasing number of passes.

Figure 2:
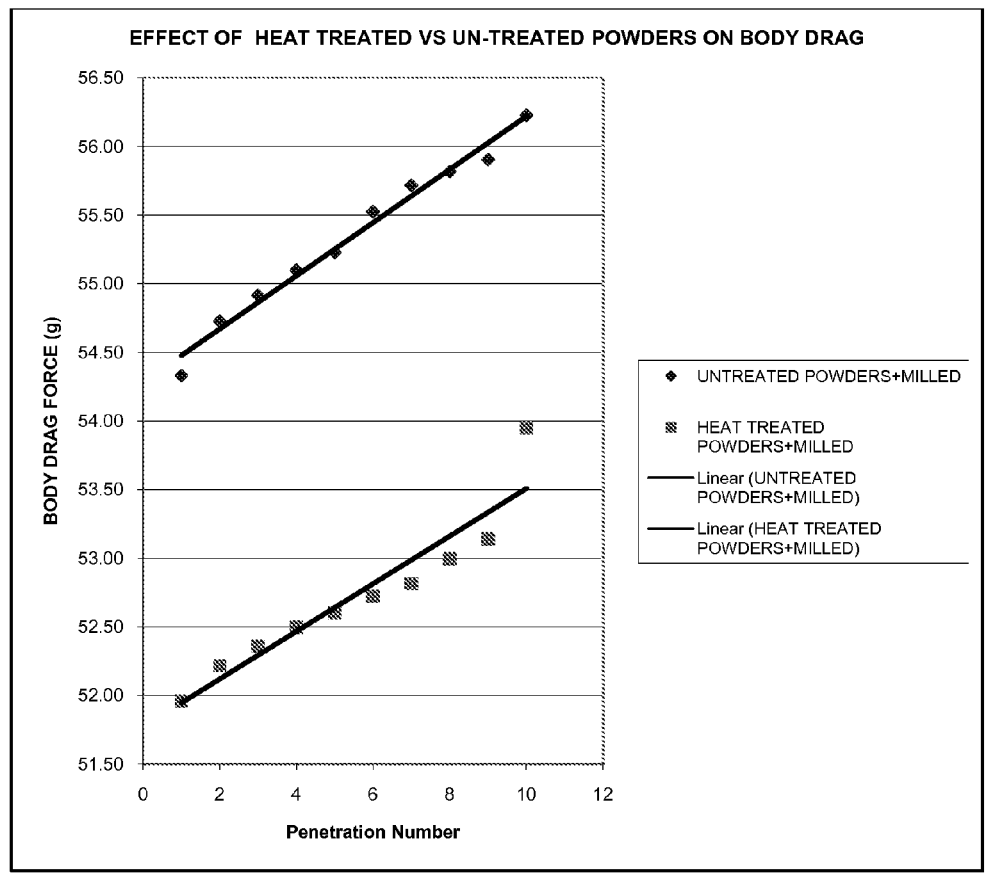
FIG. 2 is a graph illustrating the effect of heat treatment of the hydrophobic powders on the lubricity of the coating as measured by the reduction of drag forces on the needle body as it passes through a simulation substrate.

As shown in FIG. 2, the body drag force needed to penetrate through a simulation substrate with needles coated with heat treated milled hydrophobic powders was observed to be significantly lower compared to those needles coated with milled hydrophobic powders not subject to heat treatment.

Figure 3:
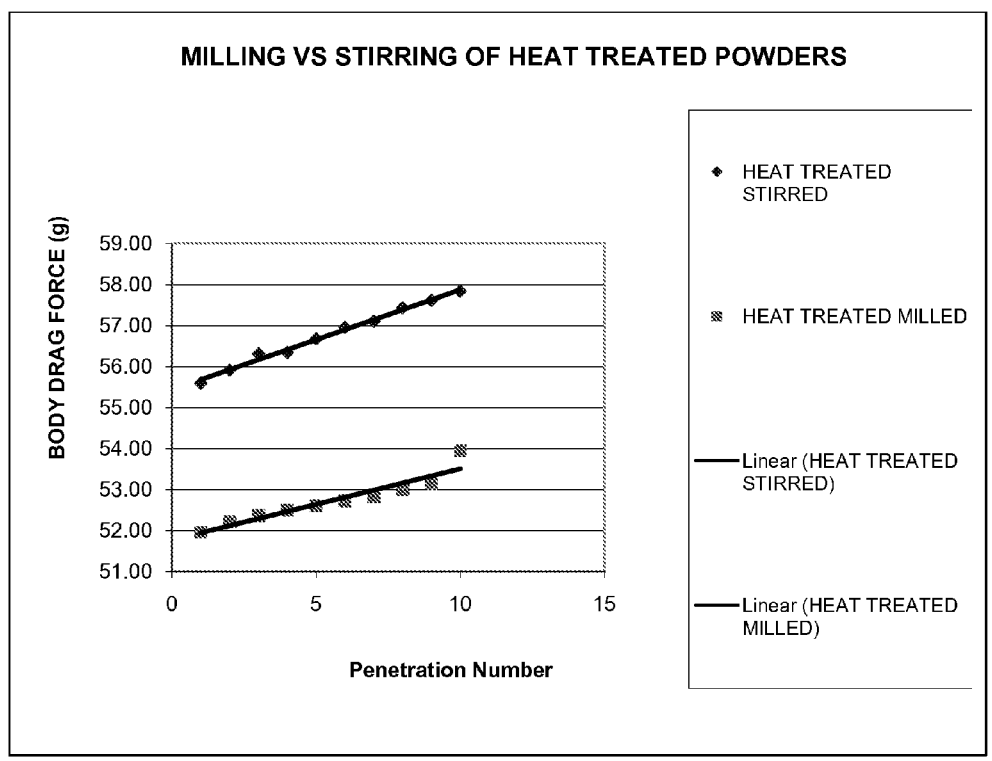
FIG. 3 is a graph comparing milling versus stirring of heat-treated hydrophobic powders measured as a reduction of body drag force of 22 mil taper point test needles.

As shown in FIG. 3, the body drag force needed to penetrate through a simulation substrate with needles coated with milled hydrophobic powders was observed to be significantly lower compared to those needles coated with stirred hydrophobic powders. Both coatings contained slip agents and were heat-treated.

Figure 4:
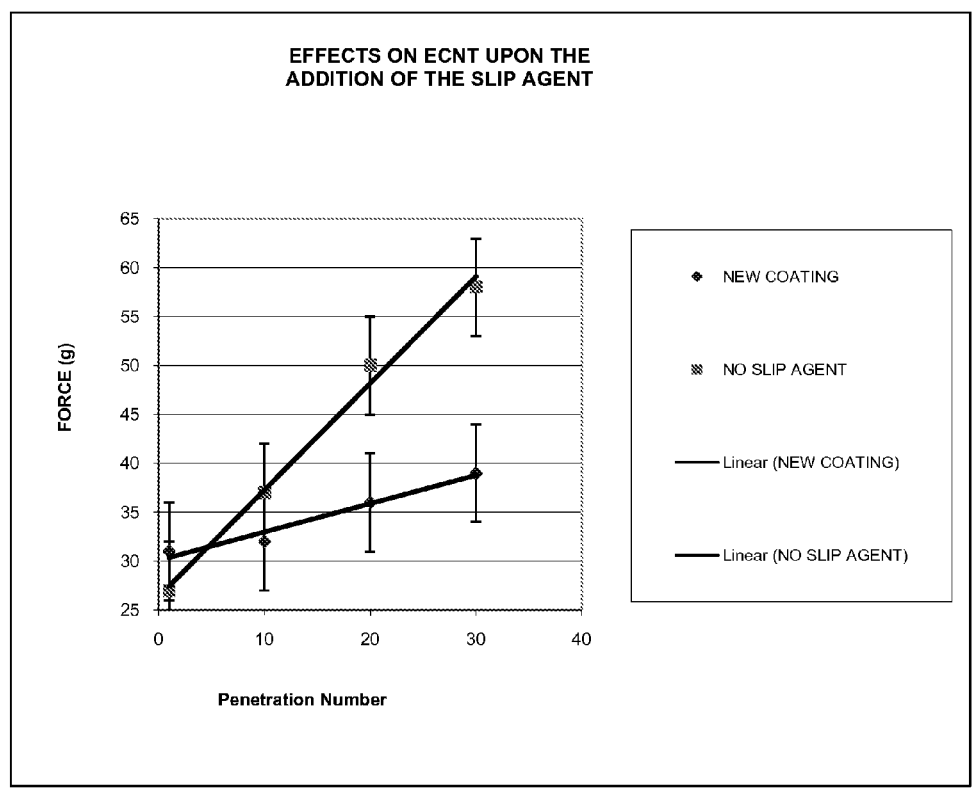
FIG. 4 is a graph illustrating the effect of the addition of the slip agent distearate polydimethylsiloxane to the coating on needle penetration performance and durability.

As shown in FIG. 4 the force needed to penetrate through a simulation substrate with needles treated with the coating of the present invention was significantly reduced compared to the needles not treated with the coating without the slip agent, distearate polydimethylsiloxane. It is noted that the reduction effect was more profound with increasing number of passes.

Although this invention has been shown and described with respect to detailed embodiments thereof, it will be understood by those skilled in the art that various changes in form and detail thereof may be made without departing from the spirit and scope of the claimed invention.

I claim:

1. A medical device having a cured lubricious coating on at least one surface, wherein the cured coating comprises:
    a silicone polymer, wherein the silicone polymer comprises polydimethylsiloxane;
    a silicone cross-linking agent, said cross-linking agent comprising methyl hydrogen polydimethyl siloxane
    a non-silicone hydrophobic polymer powder comprising particles, wherein the particles have an oxidized surface layer, said polymer comprising polypropylene;
    a slip agent; and,
    a catalyst.

2. The device of claim 1, wherein the slip agent comprises distearate polydimethyl siloxane.

3. The device of claim 1, wherein the catalyst comprises dibutyl tin dilaurate.

4. A method of coating a medical device with a lubricious coating, comprising:
    a. providing a medical device having an exterior surface;
    b. providing a coating composition, comprising:
        a silicone polymer, wherein the silicone polymer comprises polydimethylsiloxane;
        a silicone cross-linking agent, said cross-linking agent comprising methyl hydrogen polydimethyl siloxane;
        a non-silicone hydrophobic polymer powder comprising particles, wherein the particles have an oxidized surface layer, said polymer comprising polypropylene;
        a slip agent;
        a catalyst; and,
        an organic solvent;
    c. applying the coating to at least a portion of the surface of the medical device; and,
    d. curing the coating.

5. The method device of claim 4, wherein the slip agent comprises distearate polydimethyl siloxane.

6. The method of claim 4, wherein the catalyst comprises dibutyl tin dilaurate.

* * * * *